(12) United States Patent
Cohen et al.

(10) Patent No.: US 9,283,177 B2
(45) Date of Patent: *Mar. 15, 2016

(54) TOPICAL ANESTHETIC FOR RAPID LOCAL ANESTHESIA AND METHOD OF APPLYING A TOPICAL ANESTHETIC

(75) Inventors: David M. Cohen, Lauderdale By The Sea, FL (US); Eugene R. Cooper, Berwyn, PA (US)

(73) Assignee: Juventio, LLC, Chatham, NJ (US)

( * ) Notice: Subject to any disclaimer, the term of this patent is extended or adjusted under 35 U.S.C. 154(b) by 987 days.

This patent is subject to a terminal disclaimer.

(21) Appl. No.: 12/218,624

(22) Filed: Jul. 16, 2008

(65) Prior Publication Data

US 2009/0048347 A1  Feb. 19, 2009

Related U.S. Application Data

(63) Continuation-in-part of application No. 12/015,113, filed on Jan. 16, 2008, now Pat. No. 8,759,391.

(60) Provisional application No. 60/885,068, filed on Jan. 16, 2007.

(51) Int. Cl.
| | |
|---|---|
| A61K 31/164 | (2006.01) |
| A61K 9/00 | (2006.01) |
| A61K 9/06 | (2006.01) |
| A61K 31/167 | (2006.01) |
| A61K 47/02 | (2006.01) |
| A61K 47/10 | (2006.01) |
| A61K 47/38 | (2006.01) |

(52) U.S. Cl.
CPC .................. *A61K 9/0019* (2013.01); *A61K 9/06* (2013.01); *A61K 31/164* (2013.01); *A61K 31/167* (2013.01); *A61K 47/02* (2013.01); *A61K 47/10* (2013.01); *A61K 47/38* (2013.01)

(58) Field of Classification Search
CPC ..................................................... A61K 31/164
See application file for complete search history.

(56) References Cited

U.S. PATENT DOCUMENTS

| | | | |
|---|---|---|---|
| 4,091,090 A | 5/1978 | Sipos | |
| 4,552,872 A | 11/1985 | Cooper et al. | |
| 4,764,381 A | 8/1988 | Bodor et al. | |
| 5,196,410 A | 3/1993 | Francoeur et al. | |
| 5,534,242 A | 7/1996 | Henry et al. | |
| 5,534,246 A | 7/1996 | Herb et al. | |
| 5,585,398 A | 12/1996 | Ernst | |
| 5,853,732 A * | 12/1998 | Munden | 424/769 |
| 6,295,469 B1 | 9/2001 | Linkwitz et al. | |
| 6,319,913 B1 | 11/2001 | Mak et al. | |
| 6,528,086 B2 | 3/2003 | Zhang | |
| 6,579,865 B2 | 6/2003 | Mak et al. | |
| 6,635,674 B1 | 10/2003 | Kaneko et al. | |
| 6,894,078 B2 | 5/2005 | Castillo | |
| 7,273,887 B1 | 9/2007 | Wepfer | |
| 7,335,379 B2 | 2/2008 | Carrara et al. | |
| 7,504,114 B1 | 3/2009 | Kurita et al. | |
| 2003/0027833 A1 | 2/2003 | Cleary et al. | |
| 2003/0054017 A1* | 3/2003 | Castillo | 424/400 |
| 2004/0131665 A1 | 7/2004 | Wepfer | |
| 2005/0014823 A1* | 1/2005 | Soderlund et al. | 514/536 |
| 2005/0276842 A1 | 12/2005 | Zhang et al. | |
| 2006/0280783 A1 | 12/2006 | Dipietro et al. | |
| 2007/0189978 A1 | 8/2007 | Zhang et al. | |
| 2007/0269393 A1 | 11/2007 | Wepfer | |
| 2008/0176948 A1 | 7/2008 | Cohen et al. | |
| 2009/0048347 A1 | 2/2009 | Cohen et al. | |
| 2010/0016442 A1 | 1/2010 | Cohen et al. | |

FOREIGN PATENT DOCUMENTS

| | | |
|---|---|---|
| CA | 2446060 A1 | 11/2002 |
| EP | 1293203 A1 | 3/2003 |
| WO | WO 03077885 A2 * | 9/2003 |
| WO | WO-2007/031753 A2 | 3/2007 |
| WO | WO-2007/038325 A2 | 4/2007 |
| WO | WO-2007/070679 A2 | 6/2007 |
| WO | WO-2007/070695 A2 | 6/2007 |
| WO | WO-2009/026178 A2 | 2/2009 |

OTHER PUBLICATIONS

Galinsky et al., "Basic Pharmacokinetics and Pharmacodynamics," Remington: The Science and Practice of Pharmacy (Baltimore, Lippincott Williams & Wilkins, 2006), p. 1171.
Rodu et al., "Clinical and chemical properties of a novel mucosal bioadhesive agent," J Oral Pathol., vol. 17, Nos. 9-10, Abstract (1988).
Cooper, E., "Vehicle Effects on Skin Penetration," Percutaneous Absorption, R. L. Bronaugh and H. I. Maibach, Eds., Marcel Dekker, Inc., New York, 525-529 (1985).
Cooper, E.R., "Increased Skin Permeability for Lipophilic Molecules," J. Pharm. Sci., 73(8):1153-1156 (1984).
Cooper, E.R., et al., "Effect of Fatty Acids and Alcohols on the Penetration of Acyclovir Across Human Skin In Vitro," J. Pharm. Sci., 74(6):688-689 (1985).
Cooper, E.R., et al., "Skin Permeability," Methods in Skin Research, D. Skerrow and C.J. Skerrow, Eds., John Wiley and Sons, Chichester, 407-432 (1985).
Material Safety Data Sheet Cyclohexylmethanol, 99%. Fisher Scientific [online], Mar. 7, 2006 [retrieved on Apr. 20, 2008] Retrieved from the internet URL:<https://fscimage.fishersci.com/msds/46753.htm>.
Merritt, E.W., et al., "Diffusion Apparatus for Skin Penetration," J. Controlled Release, 1:161-162 (1984).

(Continued)

*Primary Examiner* — Noble Jarrell
*Assistant Examiner* — John S Kenyon
(74) *Attorney, Agent, or Firm* — Hoffmann & Baron, LLP

(57) ABSTRACT

The invention relates to a drug delivery system for the topical administration of anesthetic agents. For example, a topical anesthetic for rapid local anesthesia is provided. The topical anesthetic includes an anesthetic, volatile and non-volatile solvents, and an optional thickener. In addition, a method is taught for applying the topical anesthetic to the face of a patient without occlusion. The anesthetic is applied topically to an area for injection such that the dermatological procedure (cosmetic injections) can be performed in fifteen minutes.

40 Claims, 1 Drawing Sheet

(56) References Cited

OTHER PUBLICATIONS

Vaida, et al., "Prolongation of lidocaine spinal anesthesia with phenylephrine," Anesthesia and Analgesia, 65(7):781-785 (1986).
Williams, et al., "Benzyl Alcohol Attenuates the Pain of Lidocaine Injections and Prolongs Anesthesia," J. Dermatol Surg Oncol., 20:730-733 (1994).
International Search Report for PCT/US08/51176 dated May 20, 2008.
United States District Court Southern District of Florida, Case No. 09-cv-60284-Graham/Torres, Complaint dated Feb. 20, 2009.
United States District Court Southern District of Florida, Case No. 09-cv-60284-Graham/Torres, Defendant's Answer to Plaintiff's Complaint with Affirmative Defenses and Counterclaim dated Mar. 23, 2009.
International Search Report for PCT/US2009/004173 dated Dec. 7, 2009.

* cited by examiner

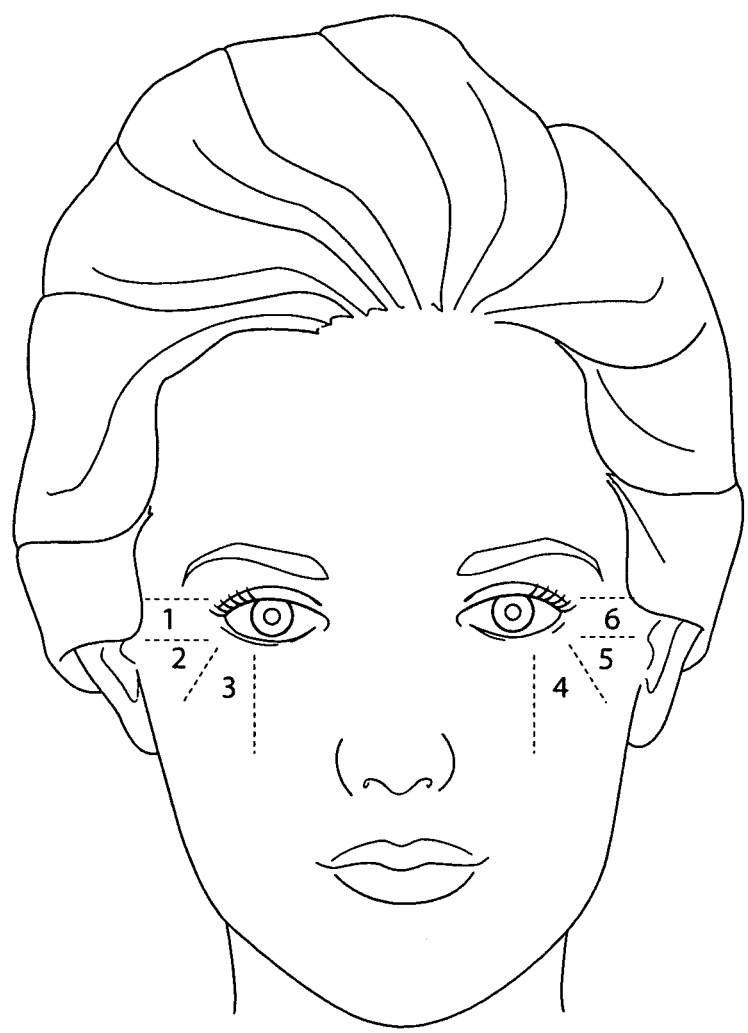

TOPICAL ANESTHETIC FOR RAPID LOCAL ANESTHESIA AND METHOD OF APPLYING A TOPICAL ANESTHETIC

RELATED APPLICATIONS

This application is a continuation-in-part of and claims priority to U.S. application Ser. No. 12/015,113, filed Jan. 16, 2008, which claims the benefit of priority to U.S. provisional application Ser. No. 60/885,068, filed Jan. 16, 2007. The disclosures of each of the foregoing applications are hereby incorporated by reference in their entirety.

BACKGROUND

Parenteral-local anesthetics cause loss of feeling before and during surgery, dental procedures (including dental surgery), or labor and delivery. These medicines do not cause loss of consciousness. Additionally, local anesthetics can be used to numb any topical pain such as an irritation, burn, scrape, cut, or insect bite.

Before performing dermatological treatments, a patient is locally anesthetized with topical anesthetics. Existing topical anesthetics used on the face take up to an hour to anesthetize effectively. The delay between application and effective anesthesia causes waiting room delays in a medical office. Thus, there exists a need to quicken the action of topical anesthetics.

SUMMARY OF INVENTION

The present invention provides a drug delivery system for topical administration of a local anesthetic agent comprising a local anesthetic agent, an alkane diol, a $C_8$-$C_{34}$ fatty acid or corresponding alcohol or ester having a melting point below 40° C., and a volatile component. In certain embodiments, the local anesthetic agent is present in an amount such that upon topical application to a surface, evaporation of the volatile component occurs such that the remaining solution is near saturation, at saturation, or above saturation with the local anesthetic agent at the temperature of the surface.

For example, the present invention provides a drug delivery system for topical administration of a local anesthetic agent comprising i) a first component which is a local anesthetic agent, such as any one of the anesthetic agents listed below, ii) a second component selected from propylene glycol or a butane diol with adjacent hydroxyl groups (e.g., butane-1,2-diol or butane-2,3-diol), iii) a third component selected from oleyl alcohol, oleic acid, ester derivatives of oleic acid such as the methyl ester, any $C_{10}$ to $C_{14}$ saturated alcohol or corresponding acid which is a liquid at room temperature, or any $C_{12}$ to $C_{22}$ mono- or poly-unsaturated or branched chain alcohol or corresponding acid which is a liquid at room temperature, and iv) a fourth component which is a volatile component, such as one or more short-chain alcohols, volatile silicones, or combinations thereof.

In certain embodiments, the local anesthetic agent is selected from any suitable local anesthetic agent. Examples of local anesthetic agents suitable for use in the drug delivery system of the present invention include lidocaine, articaine, bupivacaine, chloroprocaine, etidocaine, levobupivacaine, oxyprocaine, mepivacaine, piperocaine, prilocalne, tetracaine, procaine, dibucaine, benzocaine, dyclaine, amethocaine, lignocaine, and cinchocaine. In certain embodiments, the local anesthetic agent is lidocaine.

In certain embodiments, the drug delivery system of the present invention may further comprise a thickener, such as any suitable thickener that is soluble in the total solvent system.

The present invention further provides a method for providing a topical anesthetic effect in an animal which comprises administering to a dermal surface of an animal in need of such treatment a therapeutically effective amount of a drug delivery system according to the present invention. In certain embodiments, the animal is a human.

The present invention also provides a method of applying the drug delivery system of the present invention comprising a local anesthetic agent to the skin of a patient without occlusion. In certain embodiments, desired effects of anesthesia are evident in less than about one hour.

The present invention provides a method of utilizing the drug delivery system of the present invention, comprising applying the drug delivery system to an injection site on skin of a patient. In certain embodiments, the method further comprises the step of waiting at least fifteen minutes. In certain embodiments, the injection site is on a face of the patient. In certain embodiments, the injection site is the site of insertion of an intravenous needle or the site of a needle stick for an IM injection, an inoculation, or a blood drawing.

The present invention provides a method of utilizing the drug delivery system of the present invention, comprising applying the drug delivery system to the skin of a patient prior to a dermatological procedure. In certain embodiments, the dermatological procedure is a cosmetic injection, circumcision, a skin biopsy, removal of a pre-cancerous lesion, removal of a wart, removal of a mole, laser hair removal, laser skin resurfacing, or other cutaneous laser procedures.

DETAILED DESCRIPTION OF THE DRAWINGS

FIG. 1 shows the six zones of the lateral periocular regions for administration of dermatological injections.

DETAILED DESCRIPTION OF THE INVENTION

The present invention provides a topical anesthetic for rapid local anesthesia. In certain embodiments, the topical anesthetic provides the desired anesthetic effect in less than an hour. In certain such embodiments, the topical anesthetic includes a local anesthetic agent, a volatile component, and a non-volatile solvent. In certain embodiments, the non-volatile solvent is selected one or more solvent selected from a fatty alcohol or acid, propylene glycol, 1,2-butane diol, or 1,3-butane diol. In certain embodiments, the non-volatile solvent is a combination of an alkane diol and a $C_8$-$C_{34}$ fatty acid or corresponding alcohol or ester having a melting point below 40° C. In certain such embodiments, the non-volatile solvent is a combination of oleic acid or oleyl alcohol and propylene glycol or a butane diol with adjacent hydroxyl groups.

The present invention provides a drug delivery system for topical administration of a local anesthetic agent comprising a local anesthetic agent, an alkane diol, a $C_8$-$C_{34}$ fatty acid or corresponding alcohol or ester having a melting point below 40° C., and a volatile component. In certain embodiments, the local anesthetic agent is present in an amount such that upon topical application to a surface, evaporation of the volatile component occurs such that the remaining solution is near saturation, at saturation, or above saturation with the anesthetic agent at the temperature of the surface.

In certain embodiments of the present invention, the drug delivery system for topical administration of a local anesthetic agent provides the desired anesthetic effect in less than an hour.

In certain embodiments, the local anesthetic agent is selected from any suitable local anesthetic agent. In certain embodiments, the local anesthetic agent is a parenteral-local anesthetic. Parenteral-local anesthetics cause loss of feeling before and during surgery, dental procedures (including dental surgery), or labor and delivery. These agents do not cause loss of consciousness. Examples of local anesthetic agents suitable for use in the drug delivery system of the present invention include lidocaine, articaine, bupivacaine, chloroprocaine, etidocaine, levobupivacaine, oxyprocaine, mepivacaine, piperocaine, prilocalne, tetracaine, procaine, dibucaine, benzocaine, dyclaine, amethocaine, lignocaine, and cinchocaine. For example, the parenteral-local anesthetic agent may be selected from articaine, bupivacaine, chloroprocaine, etidocaine, levobupivacaine, lidocaine, mepivacaine, prilocalne, procaine, and tetracaine. In certain embodiments, the local anesthetic agent is lidocaine.

In certain embodiments, the local anesthetic agent (e.g., any one of the local anesthetic agents listed above) comprises between 0.001 and 20 percent by weight of the drug delivery system, such as between 0.01 and 20 percent, or 0.1 and 20 percent by weight of the drug delivery system. In certain embodiments, the local anesthetic agent (e.g., any one of the local anesthetic agents listed above) comprises between one and ten percent by weight of the drug delivery system. In certain embodiments, the local anesthetic agent (e.g., any one of the local anesthetic agents listed above) comprises between four and eight percent by weight of the drug delivery system. In certain embodiments, the local anesthetic agent (e.g., any one of the local anesthetic agents listed above) comprises less than four percent by weight of the drug delivery system. In certain embodiments, the local anesthetic agent comprises up to about four percent by weight of the drug delivery system. In certain embodiments, the local anesthetic agent is lidocaine and comprises less than four percent by weight of the drug delivery system. The U.S. Food and Drug Administration is expected to limit the concentration for over-the-counter use to four percent of lidocaine.

In certain embodiments, the alkane diol comprises a C3 or C4 alkane diol. In certain such embodiments, the alkane diol is selected from propylene glycol or a butane diol with adjacent hydroxyl groups, such as butane-1,2-diol or butane-2,3-diol. In certain embodiments, the alkane diol comprises between two and 35 percent by weight of the drug delivery system, such as between two and 30 percent by weight of the drug delivery system. In certain embodiments, the alkane diol comprises between two and eight percent by weight of the drug delivery system. In certain such embodiments, the alkane diol comprises between two and six percent by weight of the drug delivery system, such as between three and five percent by weight of the drug delivery system, such as four percent by weight of the drug delivery system. In certain embodiments, the alkane diol comprises propylene glycol. Propylene glycol, known also by the systematic name propane-1,2-diol, is an organic compound (a diol), usually a tasteless, odorless, and colorless clear oily liquid that is hygroscopic and miscible with water, acetone, and chloroform. It is manufactured by the hydration of propylene oxide.

In certain embodiments, the $C_8$-$C_{34}$ fatty acid or corresponding alcohol or ester having a melting point below 40° C. comprises a $C_8$-$C_{24}$ fatty acid or corresponding alcohol or ester having a melting point below 40° C. In certain embodiments, the $C_8$-$C_{34}$ fatty acid or corresponding alcohol or ester is liquid at room temperature (e.g., is liquid at 21-24° C.). In certain embodiments, the ester is a methyl ester. In certain embodiments the $C_8$-$C_{34}$ fatty acid or corresponding alcohol or ester having a melting point below 40° C. is selected from oleyl alcohol, oleic acid, ester derivatives of oleic acid such as the methyl ester, any $C_{10}$ to $C_{14}$ saturated alcohol or corresponding acid or ester which is a liquid at room temperature (e.g., is liquid at 21-24° C.), or any $C_{12}$ to $C_{22}$ mono- or poly-unsaturated or branched chain alcohol or corresponding acid or ester which is a liquid at room temperature (e.g., is liquid at 21-24° C.). In certain embodiments, the $C_8$-$C_{34}$ fatty acid or corresponding alcohol or ester having a melting point below 40° C. is selected from a $C_{10}$ to $C_{14}$ saturated alcohol, $C_{12}$ mono- or polyunsaturated alcohol or branched-chain alcohol that is a liquid-at-room-temperature (e.g., is liquid at 21-24° C.), a $C_{10}$ to $C_{14}$ saturated acid, and a $C_{12}$ mono- or polyunsaturated acid or branched-chain acid that is a liquid-at-room-temperature (e.g., is liquid at 21-24° C.). In certain embodiments, the $C_8$-$C_{34}$ fatty acid or corresponding alcohol or ester having a melting point below 40° C. comprises between two and 30 percent by weight of the drug delivery system. In certain embodiments, the $C_8$-$C_{34}$ fatty acid or corresponding alcohol or ester having a melting point below 40° C. comprises between two and seven percent by weight of the drug delivery system. In certain such embodiments, the $C_8$-$C_{34}$ fatty acid or corresponding alcohol or ester having a melting point below 40° C. comprises between between two and six percent by weight of the drug delivery system, such as between three and five percent by weight of the drug delivery system, such as four percent by weight of the drug delivery system. In certain embodiments, the $C_8$-$C_{34}$ fatty acid or corresponding alcohol or ester having a melting point below 40° C. comprises oleic acid or oleyl alcohol.

Generally, the fatty alcohol can be a $C_{10}$ to $C_{14}$ saturated alcohol, a $C_{12}$ to $C_{22}$ mono- or polyunsaturated alcohol or branched-chain alcohol that is a liquid at room temperature, or those same compounds in acid form. Fatty alcohols are aliphatic alcohols derived from natural fats and oils. They are the counterparts of fatty acids. They usually (but not always) have an even number of carbon atoms. They find use in the cosmetics and food industry. Fatty alcohols are a common component of waxes, mostly as esters with fatty acids but also as alcohols themselves. Those with common names include capryl alcohol (1-octanol; 8 carbon atoms); pelargonic alcohol (1-nonanol; 9 carbon atoms); capric alcohol (1-decanol, decyl alcohol; 10 carbon atoms); 1-dodecanol (lauryl alcohol; 12 carbon atoms); myristyl alcohol (1-tetradecanol; 14 carbon atoms); palmitoleyl alcohol (cis-9-hexadecan-1-ol; 16 carbon atoms, unsaturated, $CH_3(CH_2)_5CH=CH(CH_2)_8OH$); isostearyl alcohol (16-methylheptadecan-1-ol; 18 carbon atoms, branched, $(CH_3)_2CH-(CH_2)_{15}OH$); elaidyl alcohol (9E-octadecen-1-ol; 18 carbon atoms, unsaturated, $CH_3(CH_2)_7CH=CH(CH_2)_8OH$); oleyl alcohol (cis-9-octadecen-1-ol; 18 carbon atoms, unsaturated); linoleyl alcohol (9Z,12Z-octadecadien-1-ol; 18 carbon atoms, polyunsaturated); elaidolinoleyl alcohol (9E,12E-octadecadien-1-ol; 18 carbon atoms, polyunsaturated); linolenyl alcohol (9Z,12Z,15Z-octadecatrien-1-ol; 18 carbon atoms, polyunsaturated); elaidolinolenyl alcohol (9E,12E,15-E-octadecatrien-1-ol; 18 carbon atoms, polyunsaturated); ricinoleyl alcohol (12-hydroxy-9-octadecen-1-ol; 18 carbon atoms, unsaturated, diol, $CH_3(CH_2)_5CH(OH)CH_2CH=CH(CH_2)_8OH$); arachidyl alcohol (1-eicosanol; 20 carbon atoms); behenyl alcohol (1-docosanol; 22 carbon atoms); erucyl alcohol (cis-13-docosen-1-ol; 22 carbon atoms, unsaturated, $CH_3(CH_2)_7CH=CH(CH_2)_{120}H$); lignoceryl alcohol (1-tetracosanol; 24 carbon atoms); ceryl alcohol (1-hexacosanol; 26 carbon atoms); montanyl alcohol, cluytyl alcohol (1-octacosanol; 28 carbon atoms); myricyl alcohol, melissyl alcohol (1-triacontanol; 30 carbon atoms); and geddyl alcohol (1-tetratriacontanol; 34 carbon atoms).

In certain embodiments, the volatile component comprises one or more short-chain alcohols, volatile silicones, or combinations thereof. In certain embodiments, the volatile component comprises a non-aqueous volatile solvent. In certain embodiments, the short-chain alcohol is selected from the isomers of butanol, isomers of propanol, ethanol, and methanol. Alternatively, any other short-chain alcohol safe for topical administration would be appropriate. In certain embodiments, the volatile component comprises a short-chain alcohol other than methanol. In certain such embodiments, the volatile component comprises ethanol, propanol, isopropanol, butanol, or butan-2-ol. In certain embodiments, the volatile component comprises ethanol or isopropanol. In certain embodiments, the volatile component comprises a combination of one or more volatile solvents, such as a combination of one or more short-chain alcohols. In certain such embodiments, the volatile component comprises a combination of one or more volatile solvents selected from ethanol, propanol, isopropanol, butanol, and butan-2-ol. In certain embodiments, the volatile component comprises one or more volatile silicones. In certain embodiments, the volatile silicone is odorless and/or has a low heat of evaporation so it does not create a cold sensation when evaporating after being deposited on the skin. In certain embodiments, the volatile silicone comprises a volatile polydimethylsiloxane. Exemplary volatile silicone compounds include, but are not limited to, volatile, low molecular weight polydimethylsiloxane compounds. Such compounds can be either a linear or a cyclic polydimethylsiloxane compound having a viscosity from about 0.5 to about 10 cst (centistokes). In certain embodiments, the volatile silicone comprises the cyclic, volatile, low molecular weight polydimethylsiloxanes designated as cyclomethicones. Suitable cyclomethicones are available commercially under the trade names DOW CORNING 244 Fluid, DOW CORNING 245 Fluid, DOW CORNING 344 Fluid and DOW CORNING 345 Fluid from DOW CORNING Corporation, Midland, Mich., and SILICONE SF-1173 and SILICONE SF-1202 from General Electric, Waterford, N.Y. In certain embodiments, the volatile silicone comprises a linear, low molecular weight, volatile polydimethylsiloxane compound designated as hexamethyldisiloxane, decamethyltetrasiloxane, octamethyltrisiloxane, or decamethylpentasiloxane. In certain embodiments, the volatile silicone comprises hexamethyldisiloxane having a viscosity of 0.65 cST. In certain embodiments, the volatile component comprises a combination of a volatile silicone and one or more short-chain alcohol. In certain embodiments, the volatile component comprises between 60 and 90 percent by weight of the drug delivery system, such as between 60 and 85 percent by weight of the drug delivery system.

For example, the present invention provides a drug delivery system for topical administration of a local anesthetic agent comprising i) a first component which is a local anesthetic agent, such as any one of the anesthetic agents listed below, ii) a second component selected from propylene glycol or a butane diol with adjacent hydroxyl groups (e.g., butane-1,2-diol or butane-2,3-diol), iii) a third component selected from oleyl alcohol, oleic acid, ester derivatives of oleic acid such as the methyl ester, any $C_{10}$ to $C_{14}$ saturated alcohol or corresponding acid which is a liquid at room temperature (e.g., is liquid at 21-24° C.), or any $C_{12}$ to $C_{22}$ mono- or poly-unsaturated or branched chain alcohol or corresponding acid which is a liquid at room temperature (e.g., is liquid at 21-24° C.), and iv) a fourth component which is a volatile component, such as one or more short-chain alcohols, volatile silicones, or combinations thereof.

In certain embodiments, the drug delivery system of the present invention may further comprise a thickener, such as any suitable thickener that is soluble in the total solvent system. In certain embodiments, the thickener is soluble in the volatile component of the drug delivery system. Examples of thickeners that may be used in the drug delivery system of the present invention include cellulose derivatives, such as polymers comprising carboxymethyl-, hydroxyethyl-, hydroxypropyl-, hydroxypropylmethyl- or methyl-cellulose; synthetic polymers, such as those comprising polyacrylates, polymethacrylates, poly(hydroxyethyl)-, poly(hydroxypropyl)-, poly(hydroxypropylmethyl)methacrylate, polyacrylonitrile, methallyl-sulphonate, polyethylenes, polyoxiethylenes, polyethylene glycols, polyethylene glycol-lactide, polyethylene glycol-diacrylate, polyvinylpyrrolidone, polyvinyl alcohols, poly(propylmethacrylamide), poly(propylene fumarate-co-ethylene glycol), poloxamers, polyaspartamide, (hydrazine cross-linked) hyaluronic acid, and silicone; natural gums, such as those comprising alginates, carrageenan, guar-gum, gelatine, tragacanth, (amidated) pectin, xanthan, chitosan collagen, agarose; mixtures and further derivatives or co-polymers thereof and/or other pharmaceutically acceptable polymers. In certain embodiments, the drug delivery system of the present invention further comprises hydroxypropylcellulose. Pharmaceutical-grade hydroxypropylcellulose is commercially-available in a variety of molecular weights, any of which would be a suitable in the formulation of the current invention. In certain embodiments of the present invention wherein the drug delivery system further comprises a thickener, the thickener comprises between 0.1 and 3.5 percent by weight of the drug delivery system. In certain such embodiments, the thickener comprises between 2.5 and 3.5 percent by weight of the drug delivery system. The thickener helps hold the topical anesthetic on the site of the skin to be anesthetized. Other devices can be used to hold the topical anesthetic on the skin, such as a gauze pad.

In certain embodiments, the drug delivery system of the present invention comprises a thickener and a volatile silicone. In certain embodiments, the topical anesthetic comprises a thickener and a volatile silicone, wherein the thickener is hydroxypropylcellulose (HPC). In certain embodiments, the topical anesthetic comprises a thickener and a volatile silicone, wherein the thickener is hydroxypropylcellulose (HPC) which comprises between about 2.5 and about 3.5 percent by weight of the topical anesthetic.

In certain embodiments, the drug delivery system of the present invention comprises 4-8% by weight lidocaine, 2-7% by weight oleyl alcohol, 2-8% by weight propylene glycol, 2.5-3.5% by weight hydroxypropylcellulose, 60-85% by weight isopropyl alcohol, and 0-25% by weight volatile silicone. In one embodiment, the drug delivery system of the present invention comprises 4% by weight lidocaine, 4% by weight propylene glycol, 4% by weight oleyl alcohol, 3% by weight hydroxypropylcellulose, 17% by weight polydimethylsiloxane, such as hexamethyldisiloxane, and 68% by weight isopropyl alcohol.

The present invention also provides a method for administering the drug delivery system of the present invention to an animal in need of such treatment comprising applying an effective amount of the drug delivery system according to the present invention. In certain embodiments, the animal is a human.

The present invention further provides a method for providing a topical anesthetic effect in an animal which comprises administering to a dermal surface of an animal in need of such treatment a therapeutically effective amount of a drug delivery system according to the present invention. In certain such embodiments, the desired effects of anesthesia are evident in less than about one hour. In certain embodiments, the animal is a human.

The present invention provides a method of utilizing (e.g., applying) the drug delivery system of the present invention, comprising applying the drug delivery system to an injection site (e.g., a surface or area) on skin of a patient. In certain embodiments, the method further comprises the step of waiting at least fifteen minutes. In certain embodiments, the injection site is any suitable injection site. In certain embodiments, the injection site is on a face of the patient. In certain embodiments, the injection site is the site of insertion of an intravenous needle, such as for the initiation of an intravenous drip. In certain embodiments, the injection site is the site of a needle stick for an IM injection, an inoculation, or a blood drawing.

In certain embodiments, the method of utilizing the drug delivery system for topical administration of a local anesthetic agent of the present invention further comprises the step of injecting the patient on the injection site after the waiting step. In other embodiments, the method of utilizing the drug delivery system for topical administration of a local anesthetic agent of the present invention further comprises the step of injecting the patient on the injection site no more than about twenty minutes after the applying step. In still other embodiments, the method of utilizing the drug delivery system for topical administration of a local anesthetic agent of the present invention further comprises evaporating the volatile solvent during the waiting step.

The invention also encompasses a method for utilizing (e.g., applying) the drug delivery system of the present invention to anesthetize the skin of a patient without occlusion. For example, the present invention provides a method of applying the drug delivery system of the present invention comprising a local anesthetic agent to the skin of a patient without occlusion. In certain embodiments, the skin is on the face of the patient. In certain embodiments, desired effects of anesthesia are evident in less than about one hour.

The present invention provides a method of utilizing (e.g., applying) the drug delivery system of the present invention, comprising applying the drug delivery system to the skin of a patient prior to a dermatological procedure. In certain embodiments, approximately fifteen minutes after application of the drug delivery system of the present invention to the skin of a patient, a dermatological procedure can be performed. In certain embodiments, the dermatological procedure is a cosmetic injection. In certain embodiments, the dermatological procedure is circumcision. In certain embodiments, the dermatological procedure is a skin biopsy, removal of a pre-cancerous lesion, removal of a wart, or removal of a mole. In certain embodiments, the dermatological procedure is laser hair removal, laser skin resurfacing, or other cutaneous laser procedures.

The drug delivery system of the present invention also can be used for the rapid relief of pain caused by minor skin irritations, minor burns, minor cuts, and insect bites.

In certain embodiments of the present invention, more than one anesthetic agent (e.g., more than one of the anesthetic agents listed above) may be present in the drug delivery system according to the present invention. In certain embodiments of the drug delivery system of the present invention, the anesthetic agent may be a combination of more than one anesthetic agent listed above.

In certain embodiments, the drug delivery system of the present invention is specially formulated to penetrate intact skin without occlusion. In certain embodiments, the drug delivery system of the present invention is provided in a spray bottle or other suitable delivery device. In certain embodiments, the drug delivery system of the present invention is applied to the surface of the skin utilizing a cotton swab, gauze pad, or other suitable applicator.

The drug delivery system of the present invention provides faster local anesthesia than prior-art formulations that comprise four percent (4%) by weight of lidocaine. Quantitatively, it is an object of the present invention to provide a drug delivery system for topical administration of a local anesthetic agent that produces local anesthesia at least twenty percent (20%) faster than current products and lasts the duration of a subsequent procedure. The drug delivery system of the present invention provides maximum local anesthesia within fifteen to twenty minutes without occlusion. The drug delivery system for topical administration of a local anesthetic agent of the present invention allows for mild-to-deep dermal implantation of dermal fillers such as hyaluronic acid gels and Botulinum Toxin Type A. It is also believed that the drug delivery system of the present invention for topical administration of a local anesthetic agent provides sufficient local anesthesia for various dermatological office procedures such as skin biopsies and removal of pre-cancerous lesions and moles.

The term "volatile component" as used herein refers to a component (e.g., a solvent or combination of solvents) that changes readily from solid or liquid to a vapor, e.g., that evaporates readily at some temperature at or below body temperature and less readily at room temperature, such as a component that evaporates rapidly between 21 and 37° C. at atmospheric pressure.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the term "saturation" refers to the point at which a solution of a substance (e.g., a local anesthetic agent) can dissolve no more of that substance and additional amounts of it will appear as a precipitate. The phrase "near saturation" refers to a solution which is at least 90% saturated, such as 90%, 91%, 92%, 93%, 94%, 95%, 96%, 97%, 98%, or 99% saturated. The phrase "above saturation" refers to a solution which has a higher concentration of substance (e.g., a local anesthetic agent) than the concentration at which the solution is saturated (e.g., it is greater than 100% saturated).

The drug delivery system and methods of the present invention may be utilized to treat an individual in need thereof. In certain embodiments, the individual is a mammal such as a human, or a non-human mammal The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The drug delivery system of the present invention can be administered to a subject topically, for example, as a gel, foam, solution, lotion, cream, ointment or spray applied to the skin. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The drug delivery system may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the anesthetic agent which produces an anesthetic effect.

Besides the components outlined above, the drug delivery system of the present invention can also include adjuvants such as wetting agents, emulsifying and suspending agents, sweetening, flavoring, coloring, perfuming and preservative agents.

Drug delivery systems of the present invention for topical or transdermal administration include powders, sprays, ointments, pastes, creams, lotions, gels, solutions, patches and inhalants. The anesthetic agent may be mixed under sterile conditions with the other components of the drug delivery system, and with any preservatives, buffers, or propellants that may be required.

The ointments, pastes, creams and gels may contain, in addition to the anesthetic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Sprays can contain, in addition to a local anesthetic agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The drug delivery systems of the present invention may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like.

Actual dosage levels of the active ingredients in the drug delivery system may be varied so as to obtain an amount of the active ingredient that is effective to achieve the desired anesthetic response for a particular patient, composition, and mode of administration, without being toxic to the patient.

The selected dosage level will depend upon a variety of factors including the activity of the particular anesthetic agent or combination of anesthetic agents employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the drug delivery system required. For example, the physician or veterinarian could start doses of the drug delivery system or anesthetic agent at levels lower than that required in order to achieve the desired anesthetic effect and gradually increase the dosage until the desired effect is achieved. By "therapeutically effective amount" is meant the concentration of a local anesthetic agent that is sufficient to elicit the desired anesthetic effect. It is generally understood that the effective amount of the anesthetic agent will vary according to the weight, sex, age, and medical history of the subject. Other factors which influence the effective amount may include, but are not limited to, the severity of the patient's condition, the disorder being treated, the stability of the anesthetic agent, and, if desired, another type of anesthetic agent being administered with the anesthetic agent of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active anesthetic agent used in the drug delivery systems and methods of the invention will be that amount of the anesthetic agent that is the lowest dose effective to produce an anesthetic effect. Such an effective dose will generally depend upon the factors described above.

If desired, the effective daily dose of the active anesthetic agent may be administered as one, two, three, four, five, six or more sub-doses administered separately at appropriate intervals throughout the day, optionally, in unit dosage forms. In certain embodiments of the present invention, the active anesthetic agent may be administered two or three times daily. In further embodiments, the active anesthetic agent will be administered once daily.

The patient receiving this treatment is any animal in need, including primates, in particular humans, and other mammals such as equines, cattle, swine and sheep; and poultry and pets in general.

In certain embodiments, the drug delivery system of the present invention may optionally be administered conjointly with another anesthetic agent. As used herein, the phrase "conjoint administration" refers to any form of administration of two or more different anesthetic compounds such that the second compound is administered while the previously administered anesthetic compound is still effective in the body (e.g., the two compounds are simultaneously effective in the patient, which may include synergistic effects of the two compounds). For example, the different anesthetic compounds can be administered either in the same drug delivery system or in a separate formulation, either concomitantly or sequentially. Thus, an individual who receives such treatment can benefit from a combined effect of different anesthetic compounds.

This invention includes the use of pharmaceutically acceptable salts of the anesthetic compounds listed above. In certain embodiments, contemplated salts of the invention include alkyl, dialkyl, trialkyl or tetra-alkyl ammonium salts. In certain embodiments, contemplated salts of the invention include Na, Ca, K, Mg, Zn or other metal salts.

The pharmaceutically acceptable acid addition salts can also exist as various solvates, such as with water, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate, as well as coloring agents, release agents, and perfuming agents, preservatives and antioxidants can also be present in the drug delivery systems.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The present invention provides a kit comprising:
a) a drug delivery system for topical administration of a local anesthetic agent comprising i) a first component which is a local anesthetic agent, such as any one of the anesthetic agents listed above, ii) a second component selected from propylene glycol or a butane diol with adjacent hydroxyl groups (e.g., butane-1,2-diol or butane-2,3-diol), iii) a third component selected from oleyl alcohol, oleic acid, ester derivatives of oleic acid such as the methyl ester, any $C_{10}$ to $C_{14}$ saturated alcohol or corresponding acid which is a liquid at room temperature, or any $C_{12}$ to $C_{22}$ mono- or poly-unsaturated or branched chain alcohol or corresponding acid which is a liquid at room temperature, and iv) a fourth component which is a volatile component, such as one or more short-chain alcohols, volatile silicones, or combinations thereof; and
b) instructions for the administration of the drug delivery system to an individual in need thereof.

The present invention provides a kit comprising:
a) a drug delivery system for topical administration of a local anesthetic agent comprising i) a first component which is a local anesthetic agent, such as any one of the anesthetic agents listed above, ii) a second component selected from propylene glycol or a butane diol with adjacent hydroxyl groups (e.g., butane-1,2-diol or butane-2,3-diol), iii) a third component selected from oleyl alcohol, oleic acid, ester derivatives of oleic acid such as the methyl ester, any $C_{10}$ to $C_{14}$ saturated alcohol or corresponding acid which is a liquid at room temperature, or any $C_{12}$ to $C_{22}$ mono- or poly-unsaturated or branched chain alcohol or corresponding acid which is a liquid at room temperature, and iv) a fourth component which is a volatile component, such as one or more short-chain alcohols, volatile silicones, or combinations thereof, wherein the drug delivery system is packaged in a tube, such as a tube comprising 2.0 g of the drug delivery system of the present invention; and
b) instructions for the administration of the drug delivery system to an individual in need thereof.

In certain embodiments, the kit further comprises instructions for the administration of the drug delivery system conjointly with another anesthetic agent. In certain embodiments, the kit further comprises a second pharmaceutical formulation, including but not limited to a drug delivery system according to the present invention comprising a second anesthetic agent.

In certain embodiments, the invention relates to a method for conducting a pharmaceutical business, by manufacturing a drug delivery system of the present invention, or a kit as described herein, and marketing to healthcare providers the benefits of using the drug delivery system or kit for the treatment of an individual in need thereof.

In certain embodiments, the invention relates to a method for conducting a pharmaceutical business, by providing a distribution network for selling a drug delivery system of the present invention, or kit as described herein, and providing instruction material to patients or physicians for using the drug delivery system or kit for the treatment of an individual in need thereof.

In certain embodiments, the invention comprises a method for conducting a pharmaceutical business, by determining an appropriate drug delivery system of the present invention comprising an appropriate dosage of a local anesthetic agent for the treatment of an individual in need thereof, conducting therapeutic profiling of identified drug delivery systems for efficacy and toxicity in animals, and providing a distribution network for selling an identified drug delivery system as having an acceptable therapeutic profile. In certain embodiments, the method further includes providing a sales group for marketing the drug delivery system to healthcare providers.

In certain embodiments, the invention relates to a method for conducting a pharmaceutical business by determining an appropriate drug delivery system of the present invention comprising an appropriate dosage of a local anesthetic agent for the treatment of an individual in need thereof, and licensing, to a third party, the rights for further development and sale of the formulation.

EXEMPLIFICATION

Example 1

Two formulations were evaluated comprising the following components:
4% lidocaine
4% propylene glycol
4% oleyl alcohol
2 or 3% hydroxypropylcellulose
68 or 69% isopropyl alcohol (IPA)
17% hexamethyldisiloxane.

Formulation #1 contained 3% hydroxypropylcellulose (e.g., KLUCEL™) and 68% isopropyl alcohol. Formulation #2 contained 2% hydroxypropylcellulose (e.g., KLUCEL™) and 69% isopropyl alcohol. Both formulations were clear to translucent liquids. Formulation #1 was slightly thicker than Formulation #2 but both were sufficiently viscous so as not to drip when applied. Product was placed around the area of the lips with a cotton swab and then rubbed into the area. The formulations remained on the area of application while not leaving a film and were easily wiped off prior to injection.

Patient #1—Formulation #1—experienced numbness almost immediately and was able to be injected after 15 minutes exposure. No pain due to the needle stick was noted.

Patient #2—Formulation #2—experienced numbness almost immediately and was able to be injected after 15 minutes exposure. Patient indicated that the pain at injection was similar to previous procedures that utilized lidocaine/prilocalne cream sold under the brand name EMLA. However, previous procedures allowed the EMLA to remain on the skin for over 60 minutes prior to injection.

Patient #3—Formulation #1—two applications 15 minutes apart were made. Patient experienced pain on injections similar to previous injections. Again, previous procedures utilized EMLA with greater than 60 minutes exposure.

Patient #4—Formulations #1 and #2—Products were applied to the left and right side of the site to evaluate the products side-by-side. Formulation #1 was judged superior by the patient; numbness was experienced more quickly. Injections were made 15 to 20 minutes after application.

Two additional patients were evaluated. Samples were applied as per Patient #4 above. In both cases, Formulation #1 was judged superior. In addition, one patient that required removal of a growth was treated with Formulation #1 and, after 15 minutes, had no pain at the site of biopsy.

Example 2

The application of a drug delivery system according to the present invention was tested prior to the injection of 4 units of Botox® to the crow's feet wrinkles.

A topical anesthetic comprising 4% lidocaine, 4% propylene glycol, 4% oleyl alcohol, 1.75% hydroxypropylcellulose, 69.25% isopropyl alcohol (IPA), and 17% hexamethyldisiloxane was prepared for use in the following dermatological procedures.

Twelve subjects received a total of six Botox® injections at four units each in six separate zones demarcated in the lateral periocular regions bilaterally. The six zones are depicted in FIG. 1. The administration of the injections to the specific zones was randomized among the subjects. The first injection was administered at time 0 minutes in the absence of the topical anesthetic solution. Following the initial injection, the topical anesthetic solution described above was applied to the remaining 5 zones. Injections were then given at 5 minutes, 15 minutes, 25 minutes, 35 minutes, and 45 minutes following application of the anesthetic solution. Immediately following each injection, patients were asked to rank their perceived pain on the visual analog scale (VAS) from 1-10. Patients were instructed that 1 indicates "no pain", 5 indicates "moderate pain", and 10 indicates "worst pain". A ranking of 3 is generally believed to indicate minimal pain, and a ranking of two or less is generally believed to indicate almost no perceived pain.

The average pain perceived on the VAS at times 0 minutes, 5 minutes, 15 minutes, 25 minutes, 35 minutes, and 45 minutes was 5.2±2.4, 5.8±2.7, 5.0±2.6, 3.1±1.8, 1.9±1.7, and 2.7±2.2, respectively. The data shows a slight increase in perceived pain from time 0 minutes to time 5 minutes with the least amount of pain experienced at time 35 minutes.

Three subjects experienced mild burning and irritation to the skin as well as slight irritation of the eyes following application of the topical anesthetic solution to the lateral periocular regstions. However, no redness or irritation was observed.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A drug delivery system for topical administration of a local anesthetic agent comprising 4% by weight lidocaine, 4% by weight propylene glycol, 4% by weight oleyl alcohol, 3% by weight hydroxypropylcellulose, 17% by weight polydimethylsiloxane, and 68% by weight isopropyl alcohol.

2. A method for providing a topical anesthetic effect in an animal, comprising administering to a dermal surface of an animal in need of such treatment a therapeutically effective amount of the drug delivery system of claim 1.

3. The method of claim 2, wherein the animal is a human.

4. A method of applying the drug delivery system of claim 1, comprising applying the drug delivery system to an injection site on a patient.

5. The method of claim 4, further comprising the step of waiting at least fifteen minutes.

6. The method of claim 5, further comprising the step of injecting the patient on the injection site after the waiting step.

7. The method of claim 6, wherein the step of injecting the patient on the injection site occurs no more than about twenty minutes after the applying step.

8. The method of claim 4, wherein the injection site is on the skin of the patient.

9. The method of claim 4, wherein the injection site is on the face of the patient.

10. The method of claim 4, wherein the injection site is the site of insertion of an intravenous needle or the site of a needle stick for an IM injection, an inoculation, or a blood drawing.

11. A method of applying the drug delivery system of claim 1, comprising applying the drug delivery system to skin of a patient prior to a dermatological procedure.

12. The method of claim 11, wherein the dermatological procedure is a cosmetic injection, circumcision, a skin biopsy, removal of a pre-cancerous lesion, removal of a wart, removal of a mole, laser hair removal, laser skin resurfacing or other cutaneous laser procedure.

13. The method of claim 11, wherein the dermatological procedure comprises injection through skin of the patient.

14. The method of claim 11, wherein the dermatological procedure is mild-to-deep dermal implantation of a dermal filler.

15. The method of claim 6, wherein injection is through skin of the patient.

16. A drug delivery system comprising a local anesthetic agent, propylene glycol and oleyl alcohol in a ratio of 1:1 and a volatile component comprising a combination of hexamethyldisiloxane and isopropanol.

17. The drug delivery system of claim 16, wherein the local anesthetic agent is present in an amount of from 1 to 10% by weight.

18. The drug delivery system of claim 16, wherein the local anesthetic agent is selected from the group consisting of lidocaine, articaine, bupivacaine, chloroprocaine, etidocaine, levobupivacaine, oxyprocaine, mepivacaine, piperocaine, prilocalne, tetracaine, procaine, dibucaine, benzocaine, dyclaine, amethocaine, lignocaine and cinchocaine.

19. The drug delivery system of claim 16, wherein the local anesthetic agent comprises lidocaine.

20. The drug delivery system of claim 19, wherein lidocaine is present in an amount up to 4% by weight.

21. The drug delivery system of claim 16, wherein propylene glycol and oleyl alcohol are each present in an amount of from 2 to 30% by weight.

22. The drug delivery system of claim 16, wherein the volatile component is present in an amount between 60 and 95% by weight.

23. The drug delivery system of claim 16, further comprising a thickener.

24. The drug delivery system of claim 23, wherein the thickener is hydroxypropylcellulose.

25. The drug delivery system of claim 23, wherein the thickener is present in an amount between 0.1 and 3.5% by weight.

26. A method for providing a topical anesthetic effect in an animal in need thereof, comprising administering to a dermal surface of the animal a therapeutically effective amount of the drug delivery system of claim 16.

27. The method of claim 26, wherein the animal is a human.

28. The method of claim 26, wherein the drug delivery system provides an anesthetic effect in less than about 1 hour.

29. The method of claim 26, wherein the drug delivery system provides maximum local anesthesia within 15 to 20 minutes without occlusion after application thereof.

30. A method of applying the drug delivery system of claim 16, comprising applying the drug delivery system to skin of a patient at a site of injection.

31. The method of claim 30, wherein the site of injection is on the patient's face.

32. The method of claim 30, further comprising a step of waiting at least 15 minutes prior to injection.

33. The method of claim 32, further comprising the step of injecting the patient at the site of injection after the waiting step.

34. The method of claim 33, wherein the step of injecting the patient occurs no more than about twenty minutes after the applying step.

35. The method of claim 30, wherein the site of injection is the site of insertion of an intravenous needle or the site of a needle stick for an IM injection, an inoculation, or a blood drawing.

36. The method of claim 33, wherein injection is through skin of the patient.

37. A method of applying the drug delivery system of claim 16, comprising applying the drug delivery system to a patient's skin prior to a dermatological procedure.

38. The method of claim 37, wherein the dermatological procedure is a cosmetic injection, circumcision, a skin biopsy, removal of a pre-cancerous lesion, removal of a wart, removal of a mole, laser hair removal, laser skin resurfacing or other cutaneous laser procedure.

39. The method of claim 37, wherein the dermatological procedure comprises injection through skin of the patient.

40. The method of claim 37, wherein the dermatological procedure is mild-to-deep dermal implantation of a dermal filler.

\* \* \* \* \*